US009067076B2

(12) United States Patent
Nolan et al.

(10) Patent No.: US 9,067,076 B2
(45) Date of Patent: Jun. 30, 2015

(54) MANAGEMENT OF MULTIPLE STIMULATION PROGRAM GROUPS

(75) Inventors: Joseph J. Nolan, Minnetonka, MN (US); Ruth E. Bauhahn, Fridley, MN (US); Steven M. Goetz, Brooklyn Center, MN (US); Shahram Malekkhosravi, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1606 days.

(21) Appl. No.: 11/372,355

(22) Filed: Mar. 9, 2006

(65) Prior Publication Data

US 2007/0213790 A1 Sep. 13, 2007

(51) Int. Cl.
*A61N 1/36* (2006.01)
*A61N 1/372* (2006.01)

(52) U.S. Cl.
CPC ........ *A61N 1/37247* (2013.01); *A61N 1/36132* (2013.01)

(58) Field of Classification Search
USPC ................... 600/509; 607/30, 46, 48, 57, 59; 434/322, 323, 350, 362
See application file for complete search history.

(56) References Cited

U.S. PATENT DOCUMENTS

| | | | |
|---|---|---|---|
| 5,716,384 A * | 2/1998 | Snell | 607/30 |
| 5,938,690 A * | 8/1999 | Law et al. | 607/46 |
| 6,120,467 A * | 9/2000 | Schallhorn | 600/595 |
| 6,381,496 B1 * | 4/2002 | Meadows et al. | 607/59 |
| 6,584,354 B1 | 6/2003 | Mann et al. | |
| 7,082,333 B1 * | 7/2006 | Bauhahn et al. | 607/60 |
| 7,263,402 B2 * | 8/2007 | Thacker et al. | 607/46 |
| 7,266,412 B2 * | 9/2007 | Stypulkowski | 607/48 |
| 7,386,348 B2 * | 6/2008 | North et al. | 607/46 |
| 2001/0007950 A1 * | 7/2001 | North et al. | 607/59 |
| 2001/0044585 A1 * | 11/2001 | Dupree et al. | 600/509 |
| 2002/0070976 A1 * | 6/2002 | Tanner et al. | 345/810 |
| 2002/0116036 A1 | 8/2002 | Daignault, Jr. et al. | |

(Continued)

FOREIGN PATENT DOCUMENTS

| | | | | |
|---|---|---|---|---|
| WO | WO 2006/023636 A1 | | 3/2006 | |
| WO | WO 2007/102945 | * | 9/2007 | ............. A61N 1/372 |

OTHER PUBLICATIONS

Notification of Transmittal of the International Search Report and the Written Opinion for corresponding PCT Application No. PCT/US2007/001768 dated Jan. 11, 2008 (10 pgs.).

(Continued)

*Primary Examiner* — Carl H Layno
*Assistant Examiner* — Ankit Tejani
(74) *Attorney, Agent, or Firm* — Shumaker & Sieffert, P.A.

(57) ABSTRACT

The disclosure describes a method and system that allows a user to manage multiple groups of stimulation programs that provide stimulation therapy. A physician may prepare a plurality of programs, arranged in groups that each focus on one area, that the patient may evaluate in an effort to determine if any programs provide efficacious therapy. Since the patient may be evaluating many groups by using a patient programmer, managing the groups may be difficult. The patient programmer may enable the patient to hide ineffective groups to minimize the number of groups available for therapy. In addition, the programmer may allow the patient to mark each group or program as effective or ineffective, to more easily manage groups and programs during stimulation therapy. In addition, the patient may unhide a group or program if the patient desires to reevaluate a formerly hidden option.

42 Claims, 11 Drawing Sheets

(56) References Cited

U.S. PATENT DOCUMENTS

| | | |
|---|---|---|
| 2002/0119433 A1* | 8/2002 | Callender .................... 434/322 |
| 2004/0181262 A1* | 9/2004 | Bauhahn ........................ 607/48 |
| 2004/0199215 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0267330 A1 | 12/2004 | Lee et al. |
| 2005/0209655 A1* | 9/2005 | Bradley et al. ................. 607/48 |
| 2005/0216064 A1 | 9/2005 | Heruth et al. |
| 2005/0245987 A1* | 11/2005 | Woods et al. .................. 607/46 |
| 2005/0283204 A1 | 12/2005 | Buhlmann et al. |
| 2006/0020292 A1 | 1/2006 | Goetz et al. |

OTHER PUBLICATIONS

Notification of Transmittal of the International Preliminary Report on Patentability dated May 29, 2008 for corresponding PCT Application No. PCT/US2007/001768 (6 pgs.).

\* cited by examiner

MANAGEMENT OF MULTIPLE STIMULATION PROGRAM GROUPS

TECHNICAL FIELD

The invention relates to medical devices and, more particularly, to devices that deliver electrical stimulation.

BACKGROUND

Implantable medical devices (IMDs) may be used to deliver stimulation therapy to patients to treat a variety of symptoms or conditions such as chronic pain, tremor, Parkinson's disease, epilepsy, neuralgia, urinary or fecal incontinence, sexual dysfunction, obesity, or gastroparesis. An implantable medical device may deliver stimulation therapy via leads that include electrodes located proximate to the spinal cord, pelvic nerves, stomach, or within the brain of a patient. In some cases, electrodes may be integrated with an implantable pulse generator, eliminating the need for leads. In general, the implantable medical device delivers stimulation therapy in the form of electrical pulses.

A clinician selects values for a number of programmable parameters in order to define the stimulation therapy to be delivered to a patient. For example, the clinician selects an amplitude, which may be a current or voltage amplitude, and pulse width for a stimulation waveform to be delivered to the patient, as well as a rate at which the pulses are to be delivered to the patient. Programmable parameters also may include electrode combinations and polarities. Multiple programs may be created and grouped together to provide stimulation program options to treat a condition.

Programs may be evaluated at the clinic. However, evaluation of all program options within a clinic would require more time than the patient could tolerate and be very expensive in terms of clinic time and resources. For this reason, during stimulation therapy, the patient may use an external programmer to select which group or program is used to provide stimulation therapy. In this manner, the patient is able to evaluate different programs or groups to determine the most efficacious treatment option. To effectively evaluate program options, the patient may need to browse through dozens of programs when evaluating therapy options. The process is more efficient than clinic evaluation but still time-consuming.

SUMMARY

The disclosure is directed to techniques for allowing a patient to more effectively manage multiple groups of stimulation programs that provide stimulation therapy. An external programmer permits a user to select program groups for evaluation. The programmer presents the program groups in a way that distinguishes program groups that have already been evaluated and found to be ineffective from program groups that have not yet been evaluated or have been found to be effective.

The user relies on a user interface in the external programmer to view, select and activate individual programs or program groups. By distinguishing unevaluated or effective groups from ineffective groups, the patient can readily view and select program groups for further evaluation. In some embodiments, the programmer may remove ineffective program groups from a list of available program groups, mark effective or ineffective groups, or sort the list of groups to highlight program groups that have not been evaluated and program groups that have been found to be effective.

A physician may prepare multiple programs for the patient to evaluate in an effort to identify the programs that provide most efficacious therapy. However, the patient may be required to evaluate a very large number of programs, making management of the programs difficult. Providing a mechanism to distinguish program groups may be helpful in narrowing the scope of evaluation to those groups that have not yet been evaluated and/or those groups found to be effective.

In one embodiment, the disclosure provides a method comprising presenting a list of electrical stimulation program groups for selection by a user to deliver electrical stimulation therapy via an electrical stimulator, and presenting to the user a distinction between program groups that have been previously evaluated by the user and program groups that have not been previously evaluated by the user.

In another embodiment, the disclosure provides a programmer for use with an electrical stimulator, the programmer comprising a user interface that presents information to a user of the electrical stimulator, and a processor that controls the user interface to present a list of electrical stimulation program groups for selection by a user to deliver electrical stimulation therapy via an electrical stimulator, and presents to the user a distinction between program groups that have been previously evaluated by the user and program groups that have not been previously evaluated by the user.

In an additional embodiment, the disclosure provides a computer-readable medium comprising instructions to cause a processor to present a list of electrical stimulation program groups for selection by a user to deliver electrical stimulation therapy via an electrical stimulator, and present to the user a distinction between program groups that have been previously evaluated by the user and program groups that have not been previously evaluated by the user.

In a further embodiment, the disclosure provides a system comprising an implantable electrical stimulator that delivers electrical stimulation therapy to a patient, an external programmer including a user interface that presents information to a user of the electrical stimulator, and a processor that controls the user interface to present a list of electrical stimulation program groups for selection by a user to deliver electrical stimulation therapy via an electrical stimulator, and presents to the user a distinction between program groups that have been previously evaluated by the user and program groups that have not been previously evaluated by the user.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
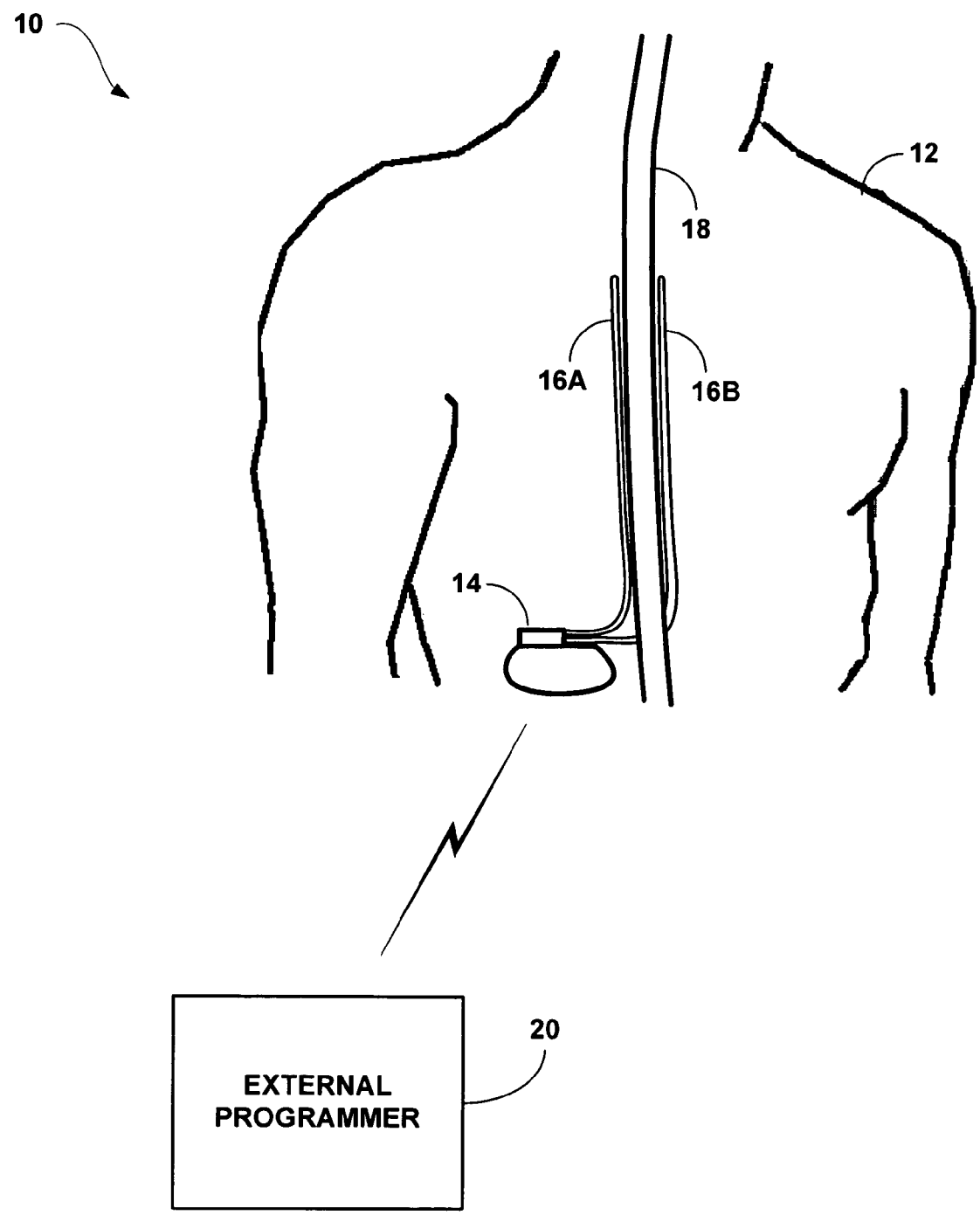
FIG. 1 is a conceptual diagram illustrating an example stimulation system with an external programmer in conjunction with a patient.

Electrical stimulation therapy may provide relief to a patient for many different conditions or disorders. Stimulation therapy is delivered based upon a variety of parameters that make up a stimulation program. Due to physiological diversity and condition differences, the parameters may vary greatly between patients. A physician may create initial parameter sets, or stimulation programs, when the patient begins stimulation therapy. For example, a clinician may initially program up to several different groups of stimulation programs containing many possible programs.

As clinic and physician resources become increasingly strained and stimulation therapies become more customized, it may be desirable that patients evaluate their stimulation therapy on their own time instead of during clinic visits. Giving the patient tools to evaluation program groups at their leisure allows the physician to shift some of the evaluation burden from within the clinic environment to outside of it and into a patient's daily life. However, physicians may desire to provide their patients with a large number of different stimulation program options in the hope that at least one of the programs, or groups of programs, are effective in treating the patient's condition.

Some patients may have problems managing all of the stimulation programs available to them. Some of these problems may include difficulty remembering which programs provide relief from their condition, which programs have not been evaluated, or spending great amounts of time navigating through many groups of stimulation programs. This disclosure describes techniques for allowing a patient to more effectively manage multiple groups of stimulation programs that provide stimulation therapy.

An external programmer permits a user to select program groups for evaluation. The programmer presents the program groups in a way that distinguishes program groups that have already been evaluated and found to be ineffective from program groups that have not yet been evaluated or have been found to be effective. A patient may rely on a user interface in the external programmer to view, select and activate individual programs or program groups. The external programmer may be referred to in this disclosure as a patient programmer, and it is contemplated that a patient may be the primary user of the programmer. However, other users such as a clinician may also make use of such a programmer, the programmer features described in this disclosure, either as a patient programmer or clinician programmer.

By distinguishing unevaluated or effective groups from ineffective groups, the patient can readily view and select program groups for further evaluation. In some embodiments, the patient programmer may remove ineffective program groups from a list of available program groups, mark effective or ineffective groups, or sort the list of groups to highlight program groups that have not been evaluated and program groups that have been found to be effective.

As one example, the programmer may hide program groups that have already been evaluated and found to be ineffective. In effect, hidden program groups are removed from the list of available program groups, thereby limiting the number of program groups available for selection by the patient. Hiding program groups may also help to generate new program groups either automatically or manually by the physician. Alternative examples of managing multiple stimulation programs may include listing the programs based upon their use, an effectiveness ranking, or only allowing a patient to move in one direction through the list until all programs have been evaluated.

As the patient continues with stimulation therapy, it may be beneficial to hide programs that no longer treat the patient effectively. The remaining unhidden groups may reduce the number of groups, or individual programs, that the patient must navigate for evaluation during stimulation therapy. Hiding ineffective groups may also provide the benefit of reminding the patient to continue evaluating untried groups in an attempt to increase therapeutic efficacy.

As used in this disclosure, the term "program" may generally refer to a combination of parameter settings, including one or more of electrode combination, electrode polarity, pulse amplitude (current or voltage), pulse width and pulse rate, used to provide stimulation therapy. A program of stimulation therapy may be delivered alone or in combination with other programs, e.g., simultaneously via multiple stimulation channels or on a time-interleaved basis via one or more stimulation channels.

The term "group," as used in this disclosure, may generally refer to a therapeutic stimulation therapy including one or more programs. For example, the programs in a group may be delivered, as described above, simultaneously or on a time-interleaved basis. In other words, the programs in a group of programs are delivered together in combination with one another.

FIG. 1 is a conceptual diagram illustrating an exemplary stimulation system 10 with an external programmer 20 in conjunction with a patient 12. In the example of FIG. 1, system 10 includes an implantable medical device (IMD) 14 that delivers stimulation therapy to patient 12 and a programmer 20 for programming IMD 14. The IMD 14 may be an implantable tissue stimulator, such as a nerve stimulator or muscle stimulator. IMD 14 delivers stimulation therapy to patient 12 via leads 16A and 16B (collectively "leads 16"). Leads 16 may, as shown in FIG. 1, be implanted proximate to spinal cord 18 of patient 12 to deliver spinal cord stimulation (SCS) therapy to patient 12.

Spinal cord stimulation may be used, for example, to reduce pain experienced by patient 12. Although an implantable IMD 14 is described for purposes of illustration, various embodiments of this disclosure also may be applicable to external medical devices that reside outside the patient's body, and deliver stimulation therapy using one of more implanted leads deployed via a percutaneous port. For example, the functions of IMD 14 may be combined with the functions of programmer 20 into one external device that provides stimulation therapy. Leads 16 may also be placed anywhere within patient 12 to address a particular condition or target stimulation site. Also, in some embodiments, IMD 14 may be a leadless microstimulator in which electrodes are carried on or near the pulse generator housing.

IMD 14 delivers electrical stimulation therapy to patient 12 according to one or more stimulation programs at a time, e.g., as a group of stimulation programs. As discussed previously, a stimulation program may specify values for a number of parameters associated with stimulation therapy delivered via an electrode configuration. The parameters may include stimulation pulse voltage or current amplitudes, pulse widths, pulse rates, electrode combinations, and other appropriate parameters such as duration or duty cycle.

Leads 16 each include one or more electrodes (not shown). The program further specifies an electrode configuration in terms of electrodes that have been selected to deliver pulses according to the program and the polarities of the selected electrodes. Not all electrodes may function at any given time. The parameters may vary in value between stimulation programs. Programs in a group may be delivered simultaneously or on a time-interleaved basis, either in an overlapping or non-overlapping manner.

IMD 14 may deliver stimulation therapy to patient 12 according to a group containing plurality of programs for a single symptom area, such as a number of leg pain programs. The plurality of programs for the single area may be a part of a program group for therapy. In addition, multiple groups may target similar areas of patient 12. IMD 14 may have different program parameters for each of the leg pain programs based on a position of patient 12, an activity rate of patient 12, or other patient parameters.

For example, IMD 14 may deliver stimulation therapy to patient 12 during a first leg pain program using a first parameter value, e.g. a voltage amplitude. In a second leg pain program, another first parameter value for the voltage amplitude may be used. Patient 12 may or may not have the ability to adjust parameter values during stimulation therapy. In many embodiments, however, it will be desirable to permit the patient 12 to adjust amplitude, pulse width and/or pulse rate, at least within adjustment limits specified by a clinician.

External programmer 20 allows a user, such as a clinician or patient 12, to evaluate and optimize the stimulation therapy provided by IMD 14. Optimization of therapy may include evaluating a plurality of stimulation programs and groups of programs to determine which parameter sets provide the most efficacious therapy. Programmer 20 presents various groups of stimulation programs for selection by a user, e.g., via a user interface including a visual display and one or more input media. Audible presentation of program groups also may be provided as an alternative or supplement to visual presentation.

Programmer 20 may distinguish groups of stimulation programs that have been evaluated by patient 12 from groups that have not been evaluated. For example, groups that have been evaluated and found to be ineffective may be distinguished from groups that have not been evaluated, or from groups that have been evaluated and found to be effective. Programmer 20 may distinguish such groups by removing ineffective program groups from a list of available program groups, marking effective or ineffective groups, or sorting the list of groups to highlight program groups that have not been evaluated and program groups that have been found to be effective.

As an illustration, ineffective program groups may be hidden from patient view, so that the patient 12 cannot select program groups that have already been evaluated and found to be ineffective. In this manner, programmer 20 narrows the number of groups available for selection by patient 12. The hidden groups may be simply hidden from view, i.e., not shown in the list presented to the patient 12, or deleted from memory. In either case, by eliminating ineffective groups, patient 12 may be able to isolate a select number of groups to continue using for evaluation of stimulation therapy.

In addition, patient 12 may be able to rank groups or individual stimulation programs as a reminder of effective therapy. For example, the ranking may be in the form of thumbs up or down, a number of stars, or some other simple ranking system. In alternative embodiments, certain groups or programs may be hidden if their ranking is below a predetermined threshold. Hiding ineffective groups, or modes for distinguishing ineffective groups from unevaluated or effective groups, reduces the complexity of the evaluation task for the patient 12, and may encourage the patient to try program groups that have not previously been evaluated, rather than inadvertently returning to program groups that have already proven ineffective. In other embodiments, patient 12 may be able to name or label a group. This method may be in addition to ranking groups. Naming a group may be construed as an indication that patient 12 likes the group, i.e., has found the group to be effective. In particular, if the patient takes the time to give a name to a group, it is likely that the patient liked the group. Names or labels may be selected from a fixed list of names, such as parts of the body, i.e., leg, arm, or back, certain activities, i.e., sitting, walking, or standing, or times of the day, i.e. morning, afternoon, or evening. Patient 12 may alternatively create a name through the use of a touchscreen keyboard, pointing device, or other input mechanism. Additionally, the name may be in the form of text and/or an icon.

Patient 12 may identify one or more stimulation groups that provide effective treatment. Programmer 20 provides a user interface (not shown in FIG. 1) for the user to select a currently effective group from one or more groups, or an unevaluated group, i.e., a group that has not yet been used. Each group may include one or more program that provides therapy to an anatomical location, to overcome a certain pain, or some other organizational scheme designed to manage the stimulation programs provided to patient 12. Patient 12 may navigate through program groups, programs within a program group, or individual stimulation programs using the user interface. The user interface may only display unhidden groups to patient 12. In some cases, patient 12 may be allowed to view all groups, with hidden groups marked as such. In this manner, patient 12 may be able to unhide a currently hidden group.

In some embodiments, the groups that patient 12 hides or unhides may enable programmer 20 to automatically generate new stimulation programs similar to programs that have been effective in treating patient 12. In this manner, programmer 20 may produce further variations or programs without the need for a physician to manually generate new programs. Programmer 20 may also be able to group these new programs according to the evaluation of hidden or unhidden programs by patient 12. Also, a clinician may review the evaluated programs and results when patient 12 returns to the clinic, permitting the clinician to formulate new program group options. In addition, the clinician may be able to reset all of the groups such that all hidden groups become unhidden. The clinician may prefer this approach if patient 12 has not fully evaluated all group options. Once patient 12 identifies effective groups, the clinician may be able to turn off the hide/unhide feature to simplify further use of programmer 20 with the selected groups. In particular, the hide-unhide feature may be disabled to simplify the user interface. Alternatively, or additionally, programmer 20 may permit the clinician to permanently delete all hidden groups, if desired.

The disclosure is not limited to the combination of leads 16 shown in FIG. 1. For example, system 10 may include only a single lead or more than two leads implanted proximate to spinal cord 18. In addition, the disclosure further contemplates the use of one or more leadless microstimulators carrying or integrating electrodes in the stimulator housing. Furthermore, the invention is not limited to the delivery of SCS therapy. For example, one or more leads 16 may extend from IMD 14 to the brain (not shown) of patient 12, and IMD 14 may deliver deep brain stimulation (DBS) therapy to patient 12 to treat tremor or epilepsy. As further examples, one or more leads 16 may be implanted proximate to the pelvic nerves (not shown) or stomach (not shown), and IMD 14 may deliver stimulation therapy to treat incontinence, obesity, gastroparesis. IMD 14 also may be used for peripheral nerve stimulation.

While the disclosure is directed to managing groups of stimulation programs or individual stimulation programs, groups of stimulation programs will be used as an example throughout the disclosure for simplicity of description. The techniques described herein may be directed to individual stimulation programs, groups of stimulation programs, or both. In each case, external programmer 20 distinguishes ineffective programs or groups from unevaluated or effective programs or groups, e.g., by hiding, marking, sorting, or the like.

Figure 2:
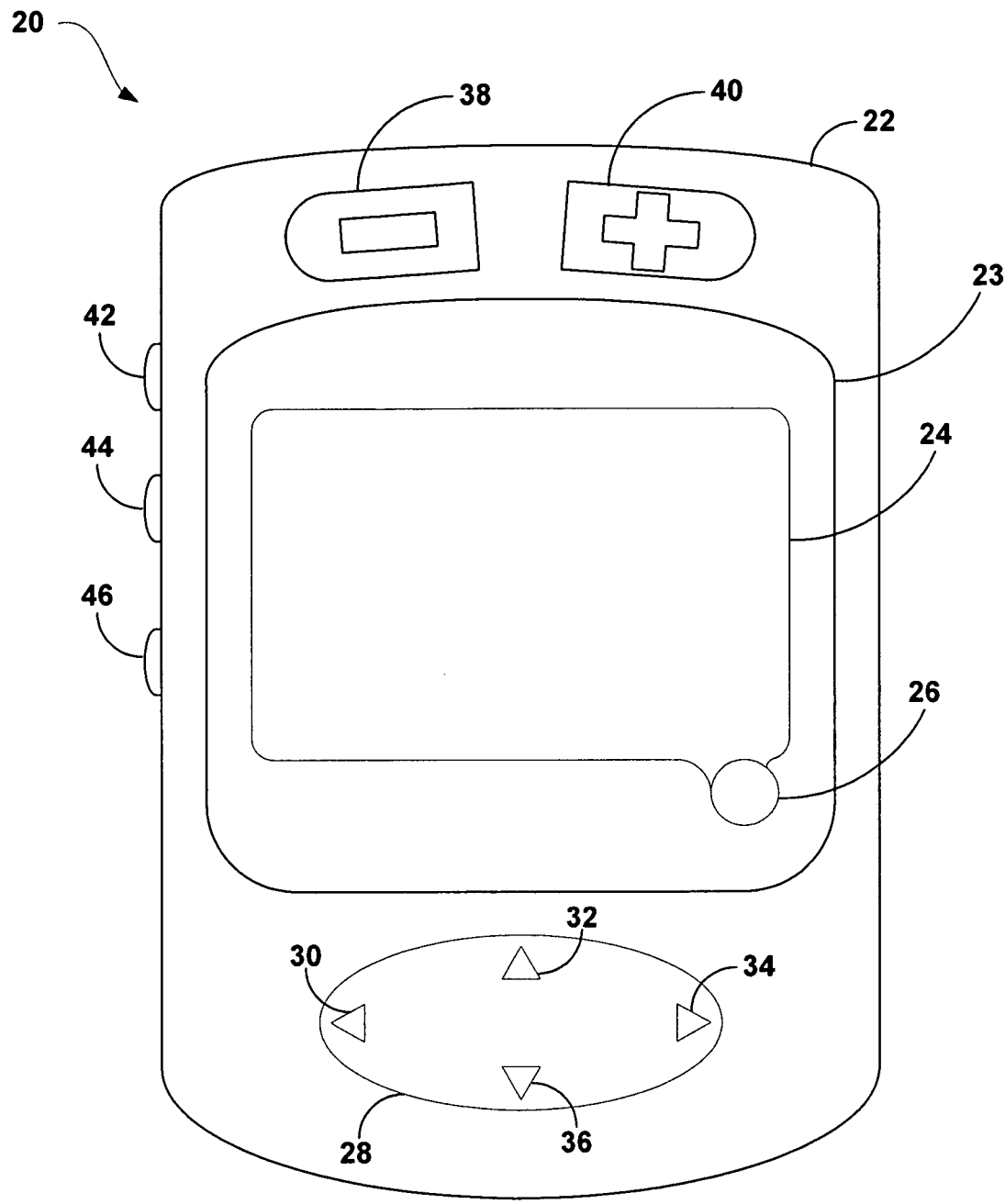
FIG. 2 is a conceptual diagram illustrating an exemplary external programmer that controls stimulation therapy.

FIG. 2 is a conceptual diagram illustrating an exemplary external programmer that controls stimulation therapy. As shown in FIG. 2, external programmer 20 provides a user interface for a user, such as patient 12, to manage stimulation therapy. Programmer 20 is protected by housing 22 which encloses circuitry necessary for the programmer to operate. Programmer 20 also includes display 24, power button 26, increase button 40, decrease button 38, hide/unhide button 46, and select buttons 42 and 44. Cover 23 protects screen 24 from being damaged during programmer 20 use. Programmer 20 also includes control pad 28 which allows a user to navigate through items displayed on display 24 in the direction of arrows 30, 32, 34 and 36.

Programmer 20 is a hand held device that may accompany patient 12 at all times. Housing 22 may be constructed of a polymer, metal alloy, composite, or combination material suitable to protect and contain components of programmer 20. In addition, housing 22 may be partially or completely sealed such that fluids, gases, or other elements may not penetrate the housing and affect components therein. Power button 26 may turn programmer 20 on or off as desired by patient 12. Power button 26 may also control the illumination level, or backlight level, of display 24. In some embodiments, power button 26 may be a knob that rotates clockwise and counter-clockwise to control programmer 20 operational status and display 24 illumination. Programmer 20 is prevented from turning off during telemetry with IMD 14 or another device to prevent the loss of transmitted data or the stalling of normal operation. Alternatively, programmer 20 and IMD 14 may include instructions which handle possible unplanned telemetry interruption, such as battery failure or inadvertent device shutdown.

Display 24 may be a liquid crystal display (LCD) or similar monochrome or color display capable of providing information to patient 12. Display 24 may provide information regarding current stimulation therapy, an active group of stimulation programs, unhidden or hidden groups, and operational status of programmer 20. Control pad 28 allows patient 12 to navigate through items displayed on display 24. Patient 12 may press control pad 28 on any of arrows 30, 32, 34, and 36 in order to move to another item on display 24 or move to another screen not currently shown on the display. In some embodiments, pressing the middle of control pad 28 may select any item highlighted in display 24. In other embodiments, scroll bars, a touch pad, scroll wheel, individual buttons, or a joystick may perform the complete or partial function of control pad 28.

Decrease button 38 and increase button 40 provide an input mechanism for patient 12. In general, decrease button 38 may decrease the value of a highlighted stimulation parameter every time the decrease button is pressed. In contrast, increase button 40 may increase the value of a highlighted stimulation parameter one step every time the increase button is pressed. While buttons 38 and 40 may be used to control the value of any stimulation parameter, buttons 38 and 40 may also control which program groups are distinguished, e.g., by hiding, marking, sorting or the like. For example, previously evaluated groups found to be ineffective may be hidden from view, while unevaluated or effective groups may be visible to the patient 12. Patient 12 may use control pad 28 to navigate to a group list screen (not shown). At the group list screen, patient 12 may press decrease button 38 to hide a group if it is unhidden or press increase button 40 to unhide a group if it is hidden. Hide/unhide button 46 may be pressed to change the screen to show all programs to patient 12 or only those programs unhidden. In other embodiments, control pad 28 may be the only input that patient 12 may use to navigate through the screens and menus of programmer 20.

Buttons 38 and 40 may also be used by patient 12 to rank a current group or program. Pressing decrease button 38 ranks the group negatively while pressing increase button 40 ranks the group positively. In the exemplary embodiment described herein, ranking one program within the group similarly ranks the group. Patient 12 may also just rank the group as a whole. In alternative embodiments, groups may be ranked by their collective ranked programs. For example, more positive rankings than negative rankings may give the group an overall positive ranking. In other embodiments, more complex ranking mechanisms may be provided to patient 12.

Select buttons 42 and 44 may be configured to perform operational functions related to stimulation therapy or the use of programmer 20. For example, buttons 42 and 44 may control the volume of audible sounds produced by programmer 20, wherein button 42 increases the volume and button 44 decreases the volume. Button 46 may be pressed to enter an operational menu that allows patient 12 to configure the user interface of programmer 20 to the desires of patient 12. For example, patient 12 may be able to select a language, backlight delay time, display 24 brightness, or other similar options. In alternative embodiments, buttons 38 and 40 may control all operational and selection functions, such as those related to audio volume or stimulation therapy.

Programmer 20 may take other shapes or sizes not described herein. For example, programmer 20 may take the form of a clam-shell shape, similar to cellular phone designs. When programmer 20 is closed, some or all elements of the user interface may be protected within the programmer. When programmer 20 is opened, one side of the programmer may contain a display while the other side may contain input mechanisms. In any shape, programmer 20 may be capable of performing the requirements described herein.

In alternative embodiments, the buttons of programmer 20 may perform different functions than the functions provided in FIG. 2 as an example. In addition, other embodiments of programmer 20 may include different button layouts or number of buttons. For example, programmer 20 may even include a single touch screen that incorporates all user interface functionality.

Figure 3:
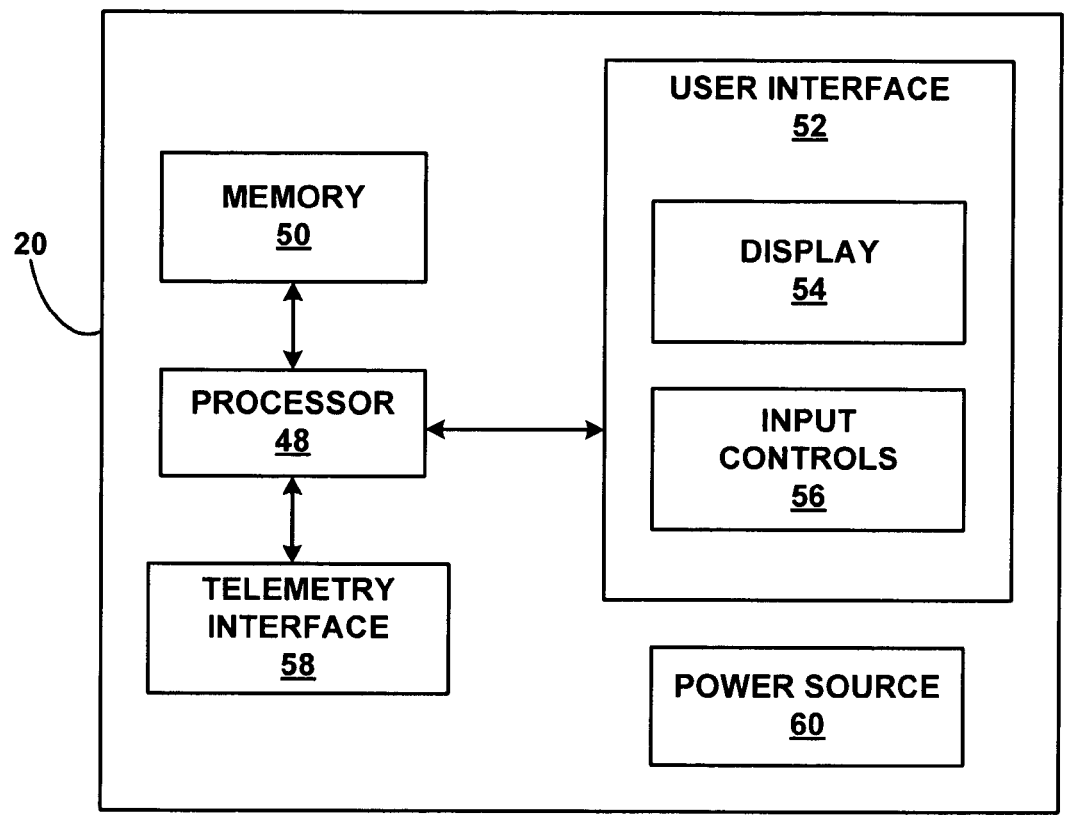
FIG. 3 is functional block diagram illustrating components of an exemplary external programmer.

FIG. 3 is functional block diagram illustrating components of an exemplary external programmer. As shown in FIG. 3, external programmer 20 includes processor 48, memory 50, user interface 52, telemetry interface 58, and power source 60. Processor 48 controls user interface 52 and telemetry interface 58, and stores and retrieves information and instructions to and from memory 50.

Programmer 20 may be used to select stimulation programs, generate new stimulation programs, modify stimulation programs through individual or global adjustments, and transmit the new programs to IMD 14. As described herein, programmer 20 allows a stimulation parameter in stimulation programs of a group to be changed by a global adjustment. Programmer 20 may be one of a patient programmer or a physician programmer. A physician programmer may include more functionality than the patient programmer to control every aspect of IMD 14, such as forcing patient 12 to evaluate unhidden groups. Additional physician programmer functionalities may include resetting use counters, adjusting parameters, viewing program or group use, and deleting unused or unwanted groups or individual programs.

A user, either a physician or patient 12, may interact with programmer 20 through user interface 52. User interface 52 includes a display 54, such as an LCD or other screen, to show information related to stimulation therapy and input controls 56 to provide input to programmer 20. Input controls 56 may include the buttons described in FIG. 2. Processor 48 monitors activity from input controls 56 and controls display 54 or stimulation function accordingly. In some embodiments, the display may be a touch screen that enables the user to select options directly from the display 24. In other embodiments, user interface 52 also includes audio circuitry for providing audible instructions or sounds to patient 12 and/or receiving voice commands from patient 12.

Memory 50 may include instructions for operating user interface 52, telemetry interface 44 and managing power source 60. Memory 50 also includes instructions for managing stimulation groups executable by processor 48 to control hide-unhide or other features of user interface 52. These instructions may include a set of rules that determine how patient 12 may hide, unhide or otherwise distinguish ineffective and effective groups. For example, these instructions may force patient 12 to evaluate a different unhidden group after a predetermined amount of evaluation time. The instructions may be defined by the desires of the clinician. In addition, memory 50 may store all stimulation programs programmed and their original and most recent set of parameter values.

Memory 50 may include any one or more of a random access memory (RAM), read-only memory (ROM), electronically-erasable programmable ROM (EEPROM), flash memory, or the like. Memory 50 may also include a removable memory portion that may be used to provide memory updates or increases in memory capacities. A removable memory may also allow sensitive patient data to be removed before programmer 20 is used by a different patient. Processor 48 may comprise any combination of one or more processors including one or more microprocessors, digital signal processors (DSPs), application specific integrated circuits (ASICs), field-programmable gate arrays (FPGAs), or other equivalent integrated or discrete logic circuitry. Accordingly, the precise structure of processor 48 is generally unimportant, provided that the processor provides appropriate processing structure, whether in hardware, software, firmware, or any combination thereof, to perform the functions ascribed herein to processor 48.

Wireless telemetry in programmer 20 may be accomplished by radio frequency (RF) communication or proximal inductive interaction of external programmer 20 with IMD 14. This wireless communication is possible through the use of telemetry interface 58. Accordingly, telemetry interface 58 may be similar to the telemetry interface contained within IMD 14. In alternative embodiments, programmer 20 may be capable of infrared communication or direct communication through a wired connection. In this manner, other external devices may be capable of communicating with programmer 20 without needing to establish a secure wireless connection.

Power source 60 delivers operating power to the components of implantable programmer 20. Power source 60 may include a battery and a power generation circuit to produce the operating power. In some embodiments, the battery may be rechargeable to allow extended operation. Recharging may be accomplished connecting power source 60 to a cradle or plug that is connected to an alternating current (AC) outlet. In addition, recharging may be accomplished through proximal inductive interaction between an external charger and an inductive charging coil within programmer 20. In other embodiments, traditional batteries may be used. In addition, programmer 20 may be directly coupled to an alternating current outlet to operate. Power source 60 may include circuitry to monitor power remaining within a battery. In this manner, display 24 may provide a current battery level indicator or low battery level indicator when the battery needs to be replaced or recharged. In some cases, power source 60 may be capable of estimating the remaining time of operation using the current battery.

Figure 4:
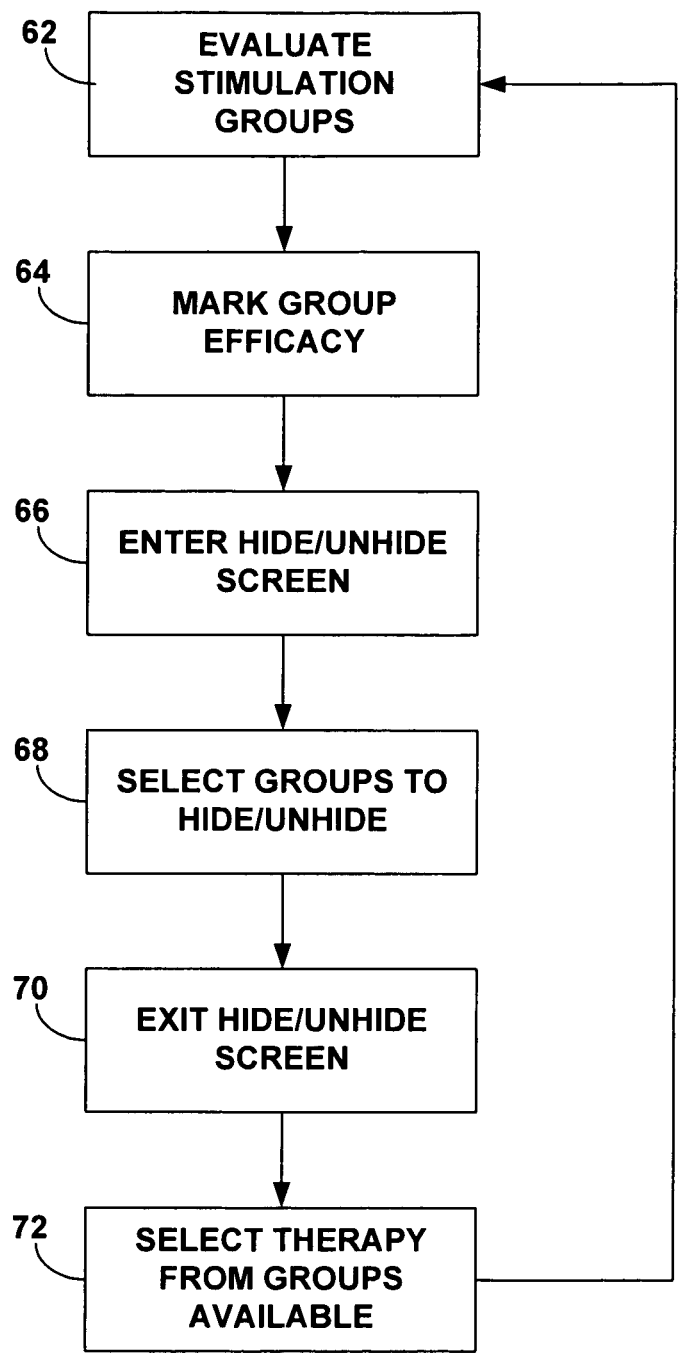
FIG. 4 is a flow diagram illustrating an exemplary technique for managing groups of stimulation programs.

FIG. 4 is a flow diagram illustrating an exemplary technique for managing groups of stimulation programs. In the example of FIG. 4, patient 12 is initially provided with a plurality of groups of stimulation programs that may provide the patient with effective therapy. Patient 12 begins stimulation therapy by evaluating different groups of stimulation programs (62). Evaluation of groups of stimulation programs includes trying each program of a group and monitoring the effects of the stimulation on the condition of patient 12. In particular, patient 12 selects a stimulation program group using programmer 20. Programmer 20 then either downloads the program group to IMD 14 or sends a command for selection of the program group within a memory within IMD 14. In response, IMD 14 applies electrical stimulation pulses according to the stimulation therapy defined by the program group.

Patient 12 marks the efficacy of the program group by applying a subjective ranking to group (64). This marking may be in the form of applying a thumbs-up or thumbs-down ranking to the group. A thumbs-up mark indicates that the group provided some therapeutic effects to patient 12, while a thumbs-down indicates that the group provided little or no therapeutic effects to the patient, or produced undesirable side effects. In other embodiments, marking group efficacy may be done by using a numeric scale or applying one or more stars to the group, where more stars indicate more efficacious therapy. In general, efficacy may be evaluated in terms of desirable therapeutic effects, such as parasthesia, and the absence of undesirable side effects.

In alternative embodiments, group marking may be done automatically based upon the use of groups by patient 12. For example, in some embodiments, if patient 12 chooses to use the group for an extended period of time or for several different times, it may be concluded that the group is generally efficacious. Group data such as the amount of time a group was used or the number of times patient 12 reverted therapy back to the group may be used by processor 48 in automatically marking a group effective or not.

After patient 12 has evaluated at least one of the available groups, patient 12 may enter a hide/unhide screen of display 24 (66). In this hide/unhide screen, all groups may be presented to patient 12 with their associated mark or rank to remind patient 12 of each group efficacy. The hide/unhide screen may also provide use information for each group displayed to patient 12. These groups may include currently unhidden or currently hidden groups. In some embodiments, the ranked groups may be sorted by rank to facilitate patient selection of a group.

In the hide/unhide screen, patient 12 may select to hide certain groups from the groups available to provide stimulation therapy (68). As one illustration, selecting to hide groups may be accomplished with decrease button 38 and selecting to unhide groups may be done with increase button 40. In some embodiments, processor 48 may automatically hide groups with marks or rankings below a physician or patient defined threshold. In this case, patient 12 may not need to enter the hide/unhide screen in order to hide groups. Automatically managing groups based upon subjective rankings or use data may be done periodically or at a time that a subjective ranking is given by patient 12.

Once patient 12 is finished hiding or unhiding groups, the patient may exit the hide/unhide screen (70), at which time memory 50 saves the current hidden and unhidden group configuration. Patient 12 may continue to select from the available unhidden groups to manage stimulation therapy (72) and continue to evaluate stimulation groups (62). Some groups are thereafter hidden from patient 12 so that the patient may view a shorter list of program group options. This process may continue throughout the therapy of patient 12, i.e., on a chronic basis, or only within an initial evaluation period, i.e., on an initial programming basis. In some embodiments, no ranking of groups is performed or any indication of group use is presented to patient 12. In this case, patient 12 may be required to remember which groups to hide from available therapeutic groups.

Figure 5:
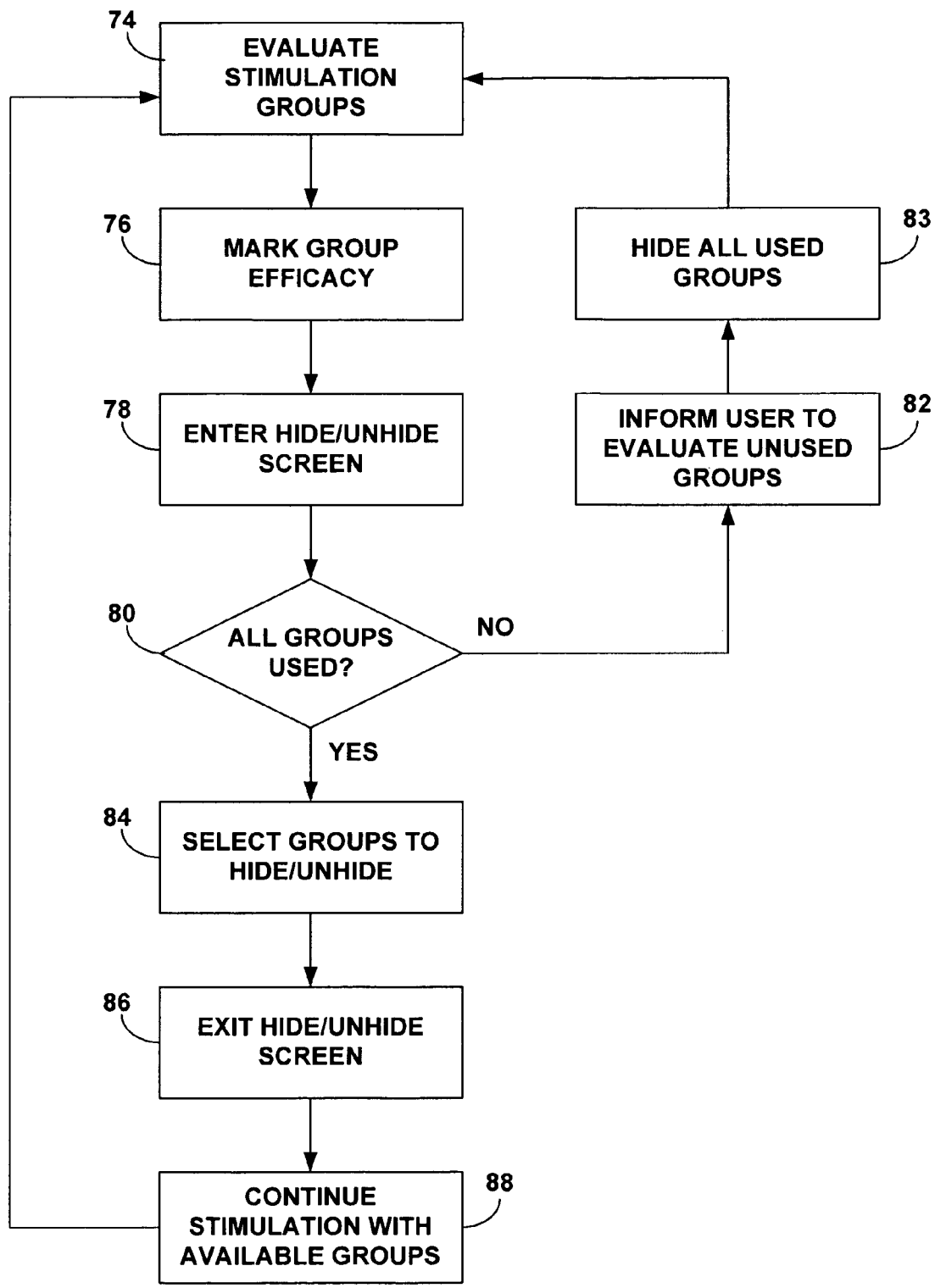
FIG. 5 is a flow diagram illustrating an exemplary technique for managing groups of stimulation programs with evaluation restrictions.

FIG. 5 is a flow diagram illustrating an exemplary technique for managing groups of stimulation programs with evaluation restrictions. In the example of FIG. 5, patient 12 is guided into trying all groups within programmer 20. Patient 12 is initially provided all stimulation groups and begins evaluating each stimulation group for efficacy (74). Similar to the example of FIG. 4, Patient 12 marks the efficacy of the group by applying a subjective ranking to group (76). This marking may be in the form of applying a thumbs-up or thumbs-down ranking to the group. A thumbs-up mark indicates that the group provided some therapeutic effects to patient 12, while a thumbs-down indicates that the group provided little or no therapeutic effects to the patient or produced undesirable side effects.

In other embodiments, marking group efficacy may be done by applying one or more stars to the group, with the more stars a group has, the more effective the group is at providing efficacious therapy. In alternative embodiments, group marking may be done automatically based upon the groups' use by patient 12. Group data such as the amount of time a group was used or the number of times patient 12 reverted therapy back to the group may be used by processor 48 in automatically marking a group effective or not.

After patient 12 has evaluated at least one of the available groups, patient 12 may desire to enter a hide/unhide screen of display 24 (78). If all groups within programmer 20 have been used (80), then patient 12 may enter the hide/unhide screen to hide or unhide groups. If not all groups have been used, display 24 delivers a message to patient 12 that informs the patient to evaluate all unused groups (82). Processor 48 subsequently hides all used groups such that patient 12 must choose another group for stimulation therapy (83) and evaluate the remaining unused groups (74). In some embodiments, processor 48 may not force patient 12 to evaluate unused programs by hiding used programs. In this case, display 24 may simply remind patient 12 to continue evaluating unused programs. In other embodiments, patient 12 may be forced to try a new group after evaluating and rating a group by only offering a "new therapy" button to the patient. In order to continue stimulation therapy, the only option available to patient 12 is the new therapy button. Once the new therapy button is pressed, programmer 20 may randomly or progressively select the next unused group for evaluation. In this manner, the process of evaluating groups is directed and controlled automatically, without the need for manual control from patient 12. This approach may provide a less complex and more controlled task flow, e.g., try new therapy, use therapy, evaluate, rate or name the therapy, and repeat until no more untried therapies remain.

A current therapy screen may display an indication for whether the active group has been evaluated or not. Programmer 20 may store the evaluated/unevaluated status of a program group, e.g., in memory 50. Alternatively, programmer 20 interfaces with IMD 14 to store the evaluated/unevaluated status of a program group in memory associated with the IMD. In this case, IMD 14 stores all program groups as well as the status of the program groups, e.g., active, evaluated, unevaluated, effective, ineffective and the like. Storage of such information in IMD 14 may be desirable so that relevant information may be stored in single place, and then be accessible via a patient programmer or a clinician programmer. In this way, there is no need for patient programmer and clinician programmer to interact with one another. Rather, the patient programmer and clinician programmer interact with IMD 14 to retrieve and store information sufficient to support hiding or unhiding of program groups during presentation via the respective programmer.

For example, when the user wants to remove a program group from a list of available program groups, the user navigates to a screen or area presented by a display of programmer 20 that permits hiding or unhiding of groups. Programmer 20 then synchronizes with IMD 14, by wireless telemetry, to record the hidden status of the selected program group in memory associated with the IMD 14. When the user wants to regain, i.e., unhide a group, the user navigates to a screen or area presented by the display of programmer 20 that permits groups to be unhidden. Programmer 20 obtains the settings for the existing group and then records the unhidden, available status of the selected program group in memory associated with IMD 14. In some embodiments, a group next to an active group may be selected to be the next active group when the programmer 20 next synchronizes with the IMD 14.

As the user navigates the program groups to select a group for evaluation, each group may include an indication as to whether it has been previously been evaluated, as well as whether the group is active or not. In some embodiments, programmer 20 may visually or audibly present a global indication indicating to the user that there are program groups remaining that have not yet been evaluated. For example, a blinking icon may be presented to indicate that unevaluated program groups are still available. Alternatively, an alarm or chime may be activated on a periodic basis to remind the patient 12 that unevaluated program groups are available. A group may be considered to be an evaluated group when it has been made active and used by IMD 14 to deliver non-zero amplitude therapy. Alternatively, programmer 20 may determine that a group has been evaluated based on usage statistics in IMD 14, or local usage statistics in patient programmer 20.

In the hide/unhide screen, all groups may be presented to patient 12 with their associated mark or rank to remind patient 12 of each group efficacy. The hide/unhide screen may also provide use information for each group displayed to patient 12. These groups may include currently unhidden or currently hidden groups. In this screen, patient 12 may select to hide certain groups from the groups available to provide stimulation therapy (84). Similar to the example of FIG. 4, selecting to hide groups may be accomplished with decrease button 38, and selecting to unhide groups may be done with increase button 40.

Once patient 12 is finished hiding or unhiding groups, the patient may exit the hide/unhide screen (86), at which time memory 50 saves the current hidden and unhidden group configuration. Patient 12 may continue to select from the available unhidden groups to manage stimulation therapy (88) and continue to evaluate stimulation groups (74). This process may continue throughout the therapy of patient 12. In some embodiments, no ranking of groups is performed or any indication of group use is presented to patient 12. In this case, patient 12 must remember which groups to hide from available therapeutic groups.

In some embodiments, instead of having patient 12 visit a hide/unhide screen, programmer 20 may perform hiding and unhiding of program groups automatically in the background. In other words, rather than requiring patient 12 to interact with a hide/unhide screen, program groups may be automatically removed from the list of available program groups (or otherwise marked, sorted or distinguished), such that the patient 12 cannot view the hidden groups the next time he attempts to select a program group for evaluation.

Figure 6:
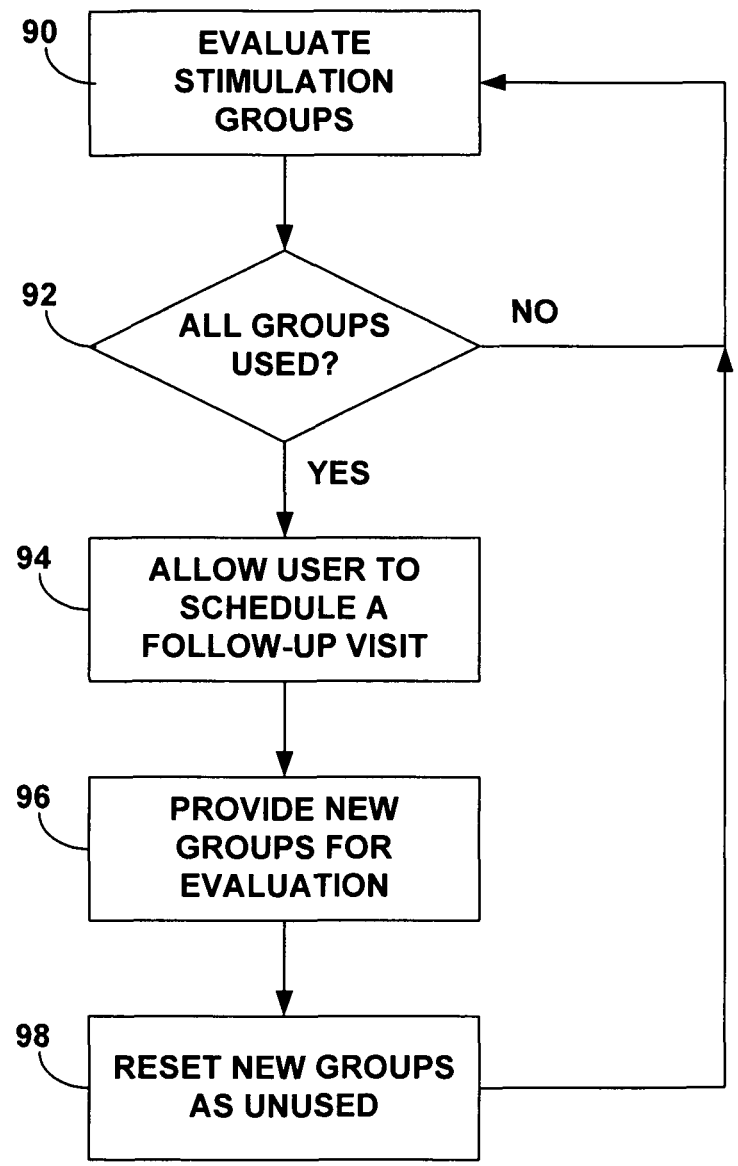
FIG. 6 is a flow diagram illustrating an exemplary technique for forcing a patient to complete evaluation before scheduling a clinic follow-up appointment.

FIG. 6 is a flow diagram illustrating an exemplary technique for forcing a patient to complete evaluation before scheduling a clinic follow-up appointment. In the example of FIG. 6, patient 12 evaluates the efficacy of groups of stimulation programs (90). Once all groups have been used (92), processor 48 may allow patient 12 to move forward with a follow-up visit or implant if in trial phase. If not all groups have been used, patient 12 must continue to use and evaluate unused groups.

Processor 48 allows patient 12 to schedule a follow-up visit with a physician once all groups have been used and evaluated (94). Programmer 20 may prohibit patient 12 from scheduling a follow-up visit before all groups have been used in order in reduce the number of unnecessary clinic visits made when an effective group may not have been evaluated. Programmer 20 may allow a visit by simply informing patient 12 to call the clinic and schedule a follow-up visit. In other embodiments, programmer 20 may deliver a code to patient 12 that the clinic may use to verify that the patient has indeed completed evaluation of all stimulation groups. In an alternative embodiment, programmer 20 may connect to a clinic device over a data connection, i.e. the internet or phone line, to verify that all groups have been evaluated by patient 12.

At the follow-up visit, a physician may provide new groups of stimulation programs to programmer 20 in place of ineffective groups, or hidden groups, as evaluated by patient 12 (96). Programmer 20 resets the new groups so that they are identified as unused groups (98) until patient 12 uses and evaluates the new groups (90). The processes of scheduling follow-up visits may be continued until patient 12 finds efficacious groups or stimulation therapy is discontinued. In some cases, stimulation therapy may be discontinued upon the first follow-up visit if no groups of stimulation programs provide a slightest amount of therapy to patient 12.

Figure 7:
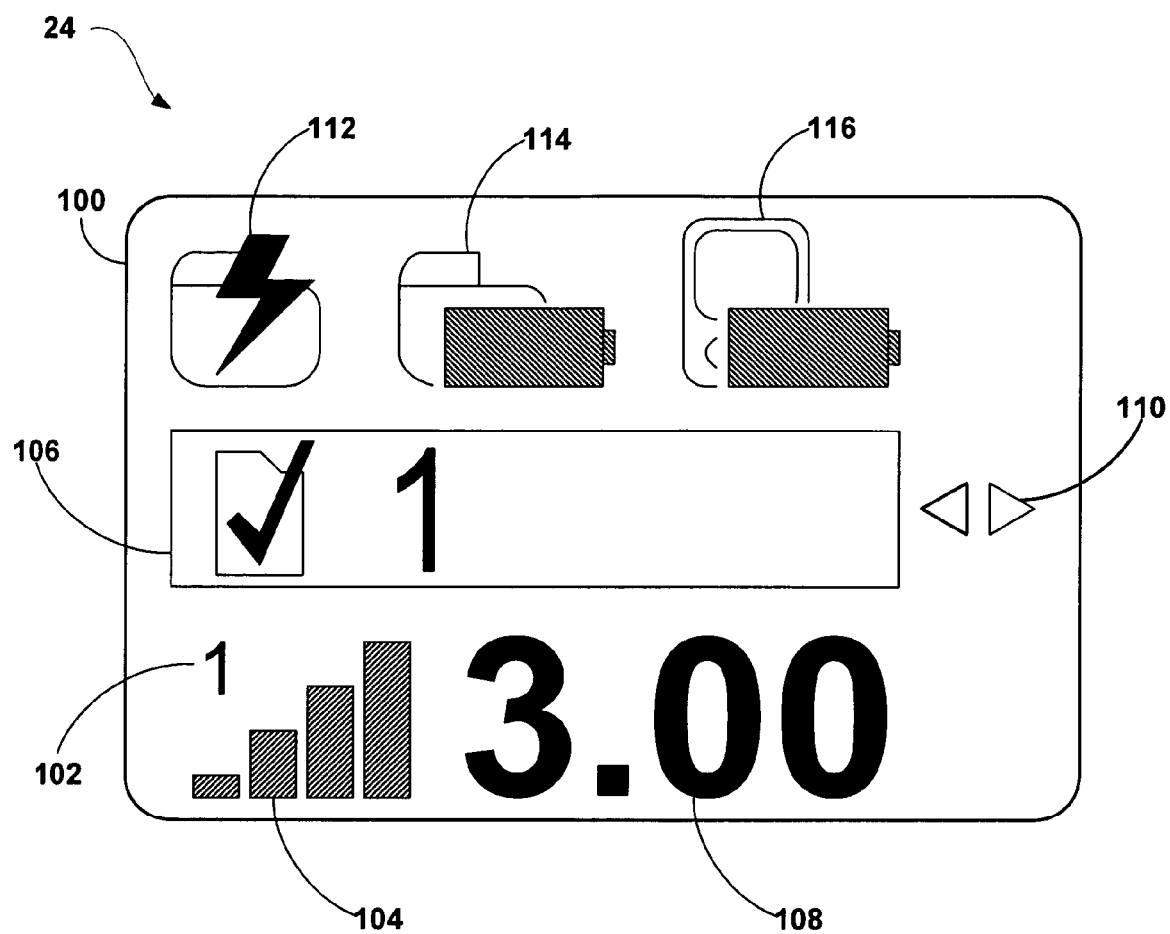
FIG. 7 is a conceptual illustration of an exemplary screen shot associated with a single stimulation program.

FIG. 7 is a conceptual illustration of an exemplary screen shot associated with a single stimulation program group. In the example of FIG. 7, display 24 of programmer 20 provides screen 100 to the user, such as patient 12. Screen 100 includes program number 102, parameter icon 104, group box 106, voltage amplitude 108, navigation arrows 110, stimulation icon 112, IMD battery 114, and programmer battery 116. Screen 100 provides information to patient 12 regarding stimulation status. More or less information may be provided to patient 12, as desired by the clinician or patient.

Program number 102 and parameter icon 104 indicate the stimulation programs with which the current group is associated. In the example of FIG. 7, the program is part of group 1. Programmer 20 may be capable of containing multiple groups. As one example, programmer 20 may store up to 26 groups that include a total of 32 programs distributed among the groups. In this example, one group may contain no more than 4 programs. In other embodiments, programmer 20 may be capable of containing more or less programs or groups of programs. Alternatively, each group may include more than 4 programs. This capability may be limited by the size or format of memory 50.

Group box 106 contains information regarding the group shown on screen 100. Group box 106 indicates that group 1 is being shown and currently selected as the group to provide stimulation by the checked file icon. In some embodiments, group box 106 may contain different information, such as a subjective ranking or amount of time group 1 has been used.

Voltage amplitude 108 displays the current voltage amplitude of the selected program 1 of group 1. Currently, the voltage amplitude is shown to be at 3.00 volts. If the voltage amplitude was at a maximum or minimum limit, a limit icon (not shown) may be displayed. In other embodiments, voltage amplitude 108 may display more or less decimal places as necessary for the stimulation therapy. In alternative embodiments where current amplitude, pulse rate, or pulse width may be adjusted, those parameter values may be displayed in place of voltage amplitude 108. In addition, patient 12 may navigate to show the value of a desired parameter and adjust it.

Stimulation icon 112 indicates the current status of stimulation therapy. Currently, the bolt is shown to indicate that stimulation is being delivered to patient 12 according to the active program group, i.e., group 1. In the case that stimulation is not being delivered, the bolt in icon 112 may not be shown. IMD battery 114 indicates the status of the battery in IMD 14, which currently indicates that the battery is fully charged, or has a full charge in the case that the battery is not rechargeable. In other embodiments of IMD battery 116, a percentage of battery life or battery life time remaining may be shown. Similar to IMD battery 114, programmer battery 116 indicates the status of the battery in programmer 20. Currently, programmer battery 116 displays that the programmer battery has a full charge. In alternative embodiments, other status indications may be used to show a percentage or time remaining of the programmer battery.

Arrows 110 provide a method for patient 12 to navigate to another screen of display 24. Patient 12 may highlight arrows 110, e.g., with a stylus or a button, and select it to move to another screen. In a similar manner, patient 12 may highlight other icons or areas of screen 100 to make modifications to that particular portion of the stimulation therapy. The components of screen 100 are provided as an exemplary screen for a single program, while other layouts or arrangements of screen 100 may be possible as well. Screen 100 may also show some elements in color if display 24 supports a color screen. In alternative embodiments, arrows 110 may not appear on screen 100, and patient 12 may simply use control pad 28 to navigate between screens.

Figure 8:
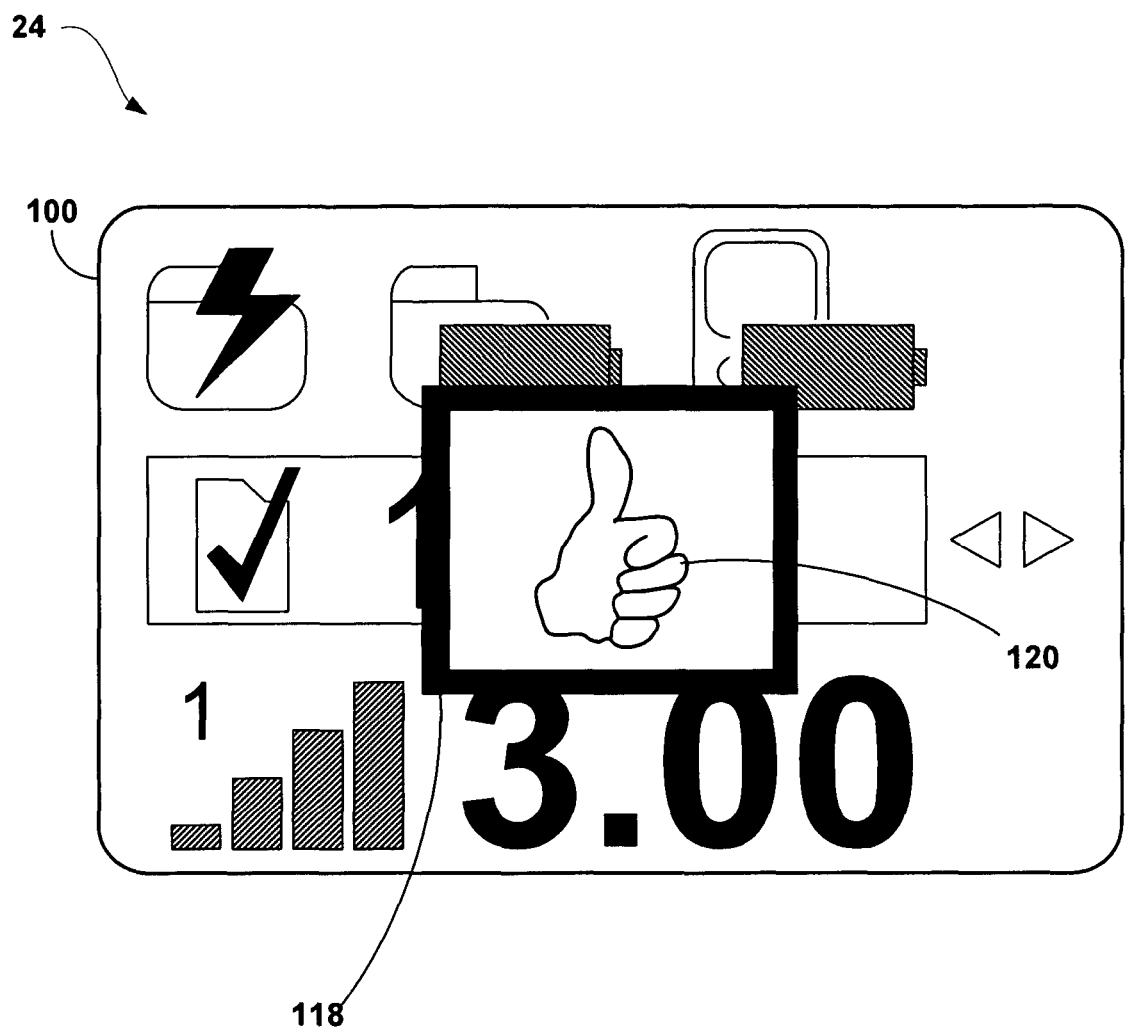
FIG. 8 is a conceptual illustration of an exemplary screen shot associated with a single stimulation program with a pop-up screen indicating a positive patient review.

FIG. 8 is a conceptual illustration of an exemplary screen shot associated with a single stimulation program with a pop-up screen indicating a positive patient review. As shown in FIG. 8, screen 100 of display 24 includes pop-up window 118 that indicates patient 12 has just made a positive evaluation of the current program by pressing increase button 40. Pop-up window 118 includes thumbs-up icon 120 that indicates to patient 12 that the patient has just stored an indication that the current program effectively provides therapy.

Figure 9:
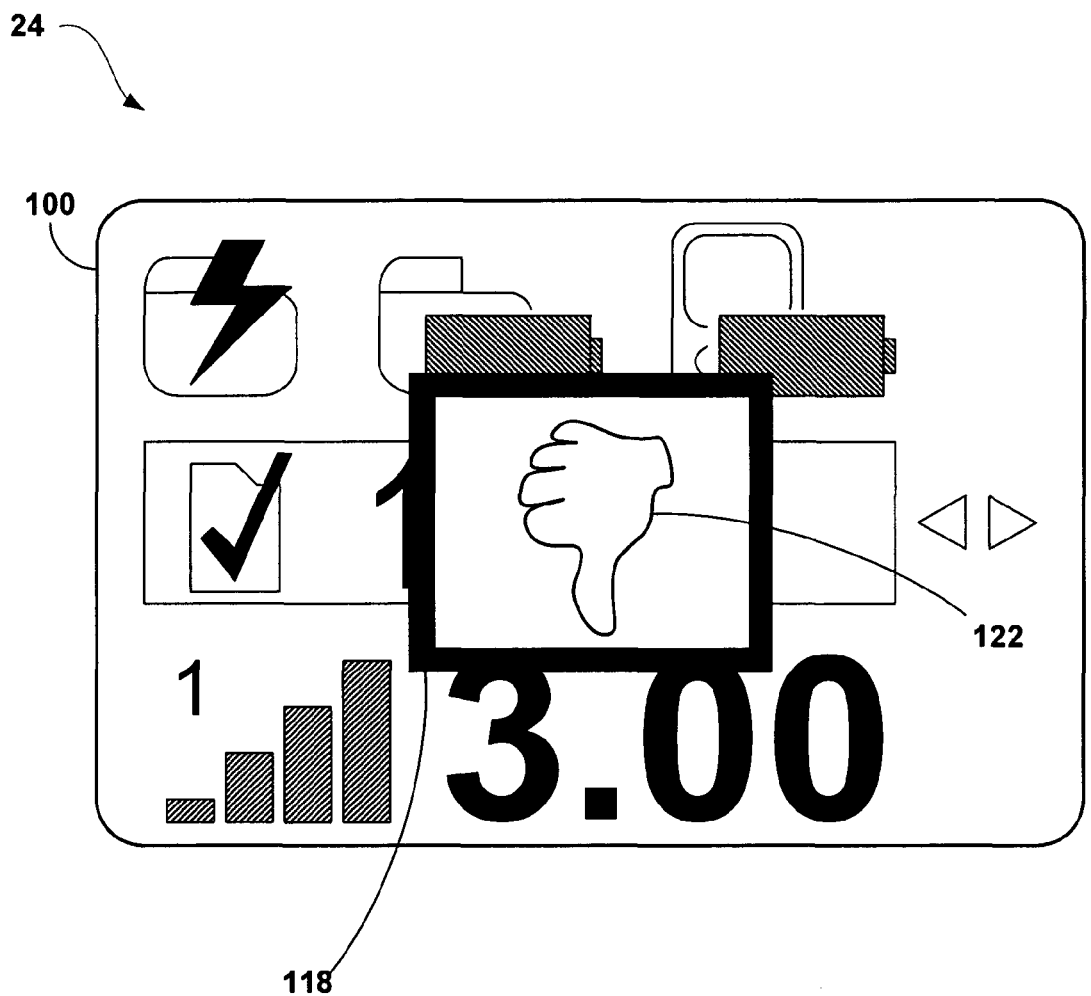
FIG. 9 is a conceptual illustration of an exemplary screen shot associated with a single stimulation program with a pop-up screen indicating a negative patient review.

FIG. 9 is a conceptual illustration of an exemplary screen shot associated with a single stimulation program with a pop-up screen indicating a negative patient review. In the example of FIG. 9, screen 100 of display 24 includes pop-up window 118 that indicates patient 12 has just made a negative evaluation of the current program group by pressing decrease button 38. Thumbs-down icon 122 is shown to indicate to patient 12 that the patient has just stored an indication that the current program group does not provide effective stimulation therapy.

In the examples of FIGS. 8 and 9, pop-up window 118 appears over screen 100 anytime that patient 12 chooses to make a ranking. The pop-up window may appear for a predetermined period of time, such as 3, 5, or 10 seconds. During the period that pop-up window 118 is presented, other operations of the stimulation therapy continue as normal. When pop-up window 118 appears, stimulation continues as previously defined because no parameters have been changed. Normal functionality of programmer 20 may be suspended when pop-up window 118 is shown. If patient 12 has mistakenly ranked the program group, patient 12 may press the other button, button 38 or 40, to correctly indicate the efficacy of the stimulation therapy delivered by the program group.

In some embodiments, pressing decrease button 38 to indicate an ineffective program group may signal processor 48 to stop stimulation with the current program group and hide the program group. In addition, processor 48 may automatically hide the entire group once the group has been deemed ineffective. Once the current stimulation has stopped, processor 48 may automatically begin another stimulation program or request that patient 12 select another stimulation program group. In other embodiments, any ranking by patient 12, positive or negative, may cause processor 48 to stop the just ranked stimulation program group and force the patient to use a new stimulation program group. In this manner, patient 12 is forced to try other program groups once the evaluation is completed.

In some embodiments, another ranking system may be used in place of the thumbs-up and thumbs-down system described herein. For example, a numerical ranking system or system including a number of stars may indicate which groups provide effective therapy. In other embodiments, pop-up window 118 may cover more or less of screen 100. Alternatively, no pop-up window 118 may appear when patient 12 makes a ranking. In addition, icons 120 or 122 may just be displayed on screen 100 when patient 12 ranks the group or program.

Figure 10:
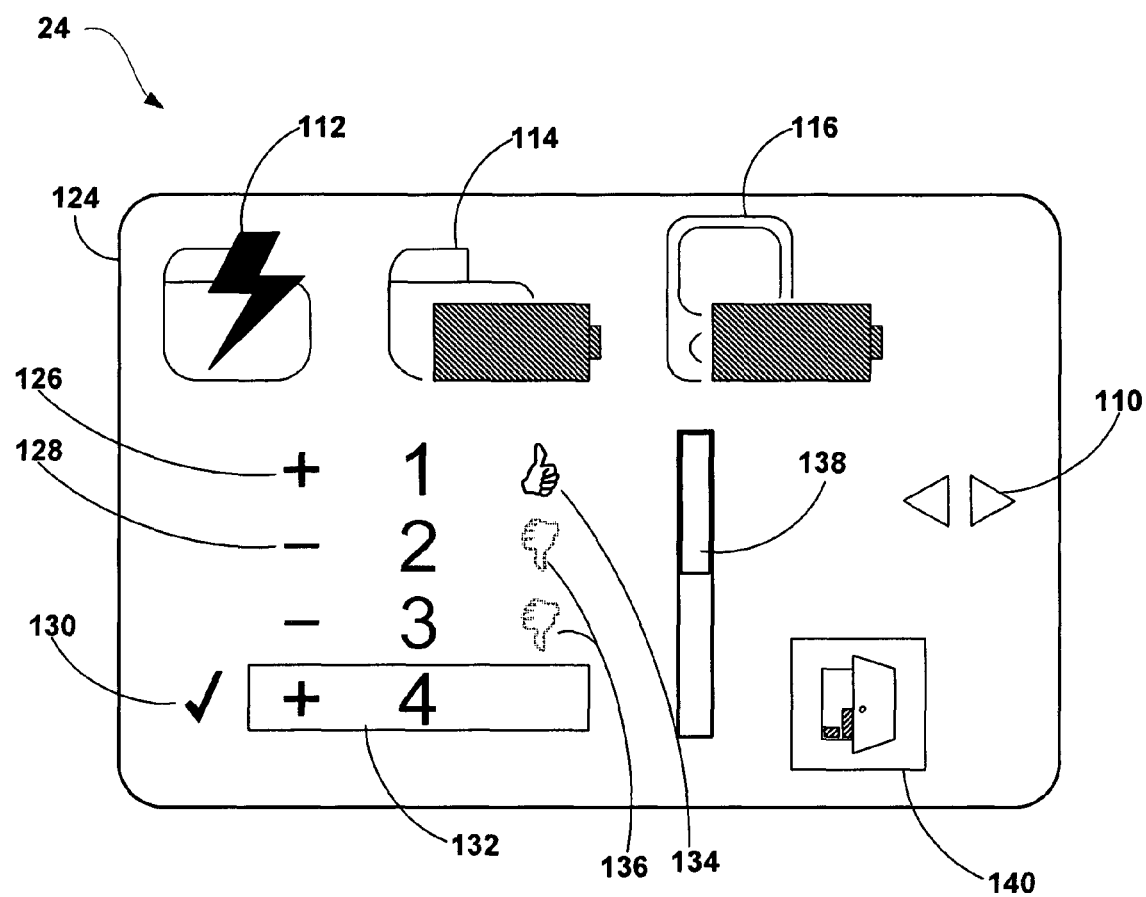
FIG. 10 is a conceptual illustration of an exemplary screen shot associated with a hide/unhide management screen.

FIG. 10 is a conceptual illustration of an exemplary screen shot associated with a hide/unhide management screen. In the example of FIG. 10, screen 124 of display 24 provides information to patient 12 regarding all groups stored on programmer 20, and indicates whether the groups are hidden or unhidden. Screen 124 includes plus 126, minus 128, check 130, select box 132, thumbs-up icon 134, thumbs-down icon 136, and scroll bar 138. Screen 124 also includes hide/unhide icon 140, arrows 110, stimulation icon 112, IMD battery 114, and programmer battery 116. Arrows 110, stimulation icon 112, IMD battery 114, and programmer battery 116 are the same elements provided in screen 100.

Check 130 indicates that program group 4 is being used to provide stimulation therapy. Plus 126 indicates that the group is unhidden while minus 128 indicates that the group is hidden. A hidden group is also shaded lighter as a further indication that the group is hidden from stimulation screens. Alternatively, a hidden group may be entirely invisible to the patient 12. Patient 12 may once again view an invisible hidden group if the patient desires to see hidden groups or the hidden and unhidden selection is reset to set all groups as unhidden. Thumbs-up icon 134 is shown next to unhidden group 1 while thumbs-down icon 136 is located next to hidden groups 2 and 3. In some embodiments, a group may be hidden or unhidden without a thumbs-up or thumbs-down icon indicating the ranking of the group. Select box 132 is highlighting group 4, and the select box may be moved to select other groups so that patient 12 may make changes to the hidden or unhidden status as well as the ranking previously given to the group. Scroll bar 138 may allow patient 12 to move to other groups not currently displayed on screen 124.

Hide/unhide icon 140 is present on screen 124 to remind patient 12 that the current screen is the hide/unhide management screen 124. Some embodiments may not include a reminder icon when allowing patient 12 to manage the hide/unhide status of stimulation groups. Alternatively, programmer 20 may automatically hide and unhide program groups.

Patient 12 may not be allowed to make changes to current stimulation therapy through screen 124. Because patient 12 may not desire to receive stimulation from hidden groups, this may be a safety feature for the patient. In alternative embodiments, patient 12 may be allowed to change stimulation therapy through screen 124 or a similar hide/unhide management screen of programmer 20. In some cases, the physician may be able to prohibit patient 12 from entering hide/unhide management screen 124, or allowing access only after all groups have been used or evaluated.

Organization and flow of hide/unhide management screen 124 may be subject to variation. In general, upon entering user input indicating a desire to access a hide/unhide mode, the user may be able to decide which group to make hidden and be able to observe an indication of which groups are hidden within an existing therapy screen that lists the program group options. The user can then scan the groups, observe the hidden/unhidden indications, and decide whether to take action to hide or unhide selected groups. Then, the user would exit the hide/unhide mode and return to normal operation, leveraging the user's familiarity with group navigation and selection.

Alternatively, the hide/unhide screen may be a new screen to which the user navigates when he wants to access the high/unhide mode. In the hide/unhide screen, as shown in FIG. 10, multiple groups may be shown with their hide/unhide status, and changes as described by the user. As a further alternative, programmer 20 may present two new screens, one to hide groups and another to unhide them. In both screens, the user is able to browse through the list of groups based on the criteria of the screen. For example, in the hide screen, only unhidden groups are displayed. Multiple groups can be hidden or unhidden. In this case, there is no actual hide/unhide mode. Rather, the ability to hide and unhide is a characteristic of the particular screen to which the user navigates. In some cases, the user can also turn therapy on/off in either of the added screens. When a user decides to hide a group, an indication may be displayed to let the user know that the group is slated to be hidden upon exiting of the hide or unhide screen, as applicable.

Figure 11:
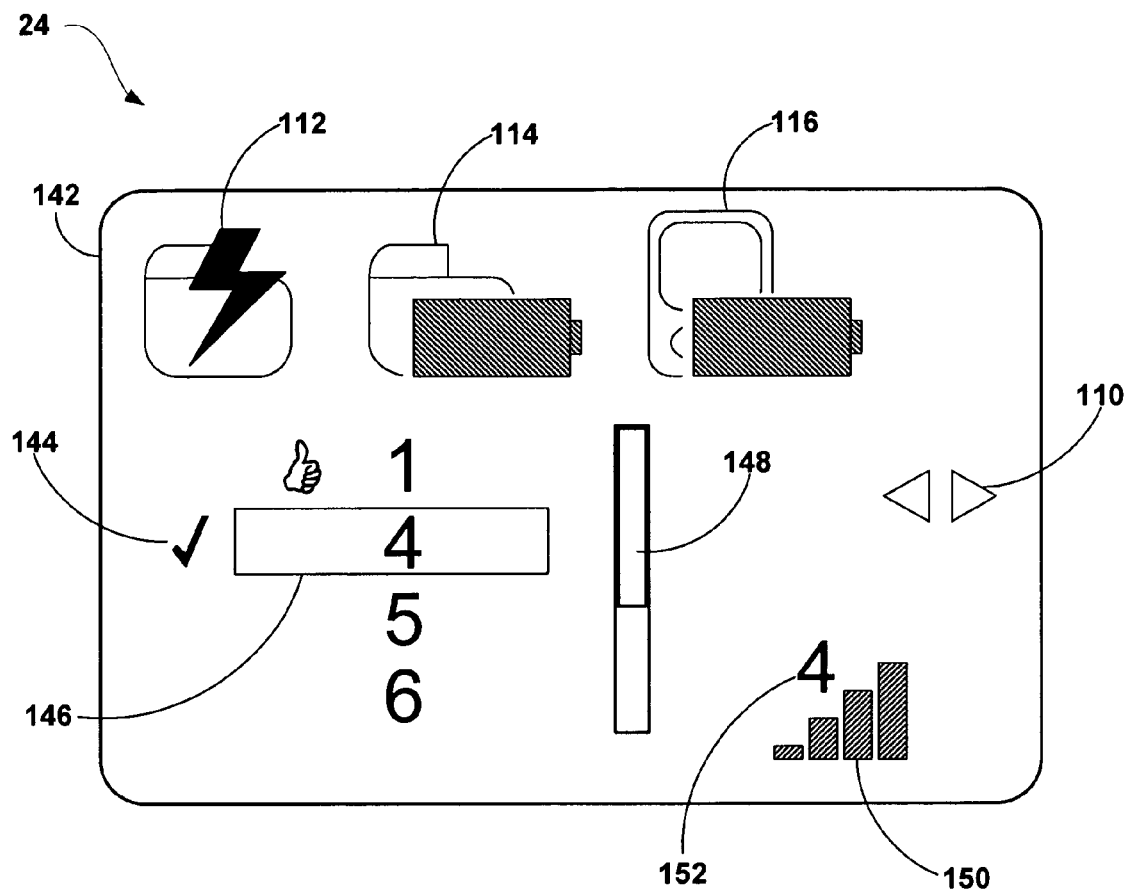
FIG. 11 is a conceptual illustration of an exemplary screen shot associated with a group display screen showing only allowed groups.

FIG. 11 is a conceptual illustration of an exemplary screen shot associated with a group display screen showing only allowed groups. In the example of FIG. 11, screen 142 of display 24 provides information to patient 12 regarding only unhidden groups stored on programmer 20. In this case, all hidden groups are not visible to the user. In this manner, ineffective groups are eliminated from the list of choices available to the patient 12. Screen 142 includes check 144, select box 146, scroll bar 148, parameter icon 150 with program number 152. Screen 124 also includes arrows 110, stimulation icon 112, IMD battery 114, and programmer battery 116, similar to screens 100 and 124.

Check 144 indicates that group 4 is currently being used to provide stimulation therapy. Parameter icon 150 and program number 152 also indicate that group 4 is being used to provide stimulation therapy. Select box 146 may be moved with control pad 28 to highlight any group to change stimulation therapy when programmer 20 is connected to IMD 14. In addition, patient 12 may use select box 146 to highlight a particular group and make a ranking with a thumbs-up or thumbs-down. Patient 12 may navigate through unhidden groups on screen 142 with scroll bar 148. Some embodiments may allow a negatively ranked group to remain unhidden until patient 12 directly hides that group.

Screen 142 may include a different arrangement or layout of the elements shown in the example of FIG. 11. In addition, more or less elements may be provided to tailor the look and operation of programmer 20 to the stimulation therapy or patient 12. Some patients may desire less control and ease of use while other patients may desire complete control over their stimulation therapy.

Screen 142 allows the user to scan all the groups that have been programmed by the clinician but have not been evaluated by the patient. By allowing the user to scan which programs have not been evaluated, the user can quickly select and activate them for evaluation. Group hide/unhide will minimize the time it takes to navigate through the group list by allowing the user to non-permanently remove groups from the list. Removed groups may be deleted from programmer 20, or alternatively, are not deleted, and instead are simply hidden from view.

In general, programmer 12 facilitates the evaluation of multiple stimulation program group choices by a patient 12. Should a clinician want to try a large number of groups, evaluating the groups at the clinic would take longer than the patient could tolerate and cost the clinic in terms of time and resources. Giving the patient 12 tools to try groups at his or her leisure allows the physician to shift some of the evaluation burden from within the clinic environment to outside of it and into a patient's daily life. In order for the patient 12 to reasonably evaluate a large number of groups, programmer 20 permits the patient to concentrate primarily or exclusively on groups that are effective. Ineffective groups are removed, marked, sorted or otherwise distinguished from unevaluated or effective groups in order to make efficacious group selection easier. This feature permits the patient 12 to more efficiently navigate through groups that have proven efficacy or have not yet been evaluated. In summary, programmer 20 enables the patient 12 to readily distinguish groups that have been evaluated from those that have not, and navigate to unevaluated or efficacious groups more quickly.

Although the disclosure may be especially applicable to the simulation of the spinal cord, the invention alternatively may be applied more generally to any type of stimulation wherein groups of stimulation programs or individual stimulation programs may be hidden or unhidden to efficiently manage stimulation therapy. As examples, cortical brain stimulation, deep brain stimulation, sacral or pudendal nerve stimulation, or dorsal root stimulation may benefit from programmer 20 described herein.

Various embodiments of the described invention may include processors that are realized by microprocessors, Application-Specific Integrated Circuits (ASIC), Field-Programmable Gate Arrays (FPGA), or other equivalent integrated logic circuitry. The processor may also utilize several different types of storage methods to hold computer-readable instructions for the device operation and data storage. These memory and storage media types may include a type of hard disk, random access memory (RAM), or flash memory, e.g. CompactFlash, SmartMedia, or Secure Digital (SD). Each storage option may be chosen depending on the embodiment of the invention. While IMD 14 may contain permanent memory, external programmer 20 may contain a more portable removable memory type to enable easy data transfer or offline data analysis.

Many embodiments of the disclosure have been described. Various modifications may be made without departing from the scope of the claims. These and other embodiments are within the scope of the following claims.

The invention claimed is:

1. A method comprising:
presenting, by a display, a list of electrical stimulation program groups for selection by a patient to deliver electrical stimulation therapy via an electrical stimulator; and
automatically hiding, by a processor that controls the display, from the list of electrical stimulation program groups, program groups that have been previously evaluated by the patient.

2. The method of claim 1, further comprising hiding one of the program groups in response to patient input requesting that the program group be hidden.

3. The method of claim 1, further comprising deleting the hidden program groups in response to patient input requesting that the hidden program groups be deleted.

4. The method of claim 1, further comprising unhiding one of the program groups in response to patient input requesting that the program group be unhidden.

5. The method of claim 1, further comprising unhiding all of the hidden program groups in response to patient input requesting that the program groups be reset.

6. The method of claim 1, further comprising preventing the patient from selecting one of the hidden program groups for delivery of stimulation therapy.

7. The method of claim 1, further comprising permitting the patient to select unhidden program groups for delivery of stimulation therapy.

8. The method of claim 1, further comprising receiving patient input indicating a degree of efficacy of one or more of the evaluated program groups, and presenting an indication of the degree of efficacy to the patient via a display.

9. The method of claim 8, further comprising navigating to a next program group that has not been previously evaluated by the patient and activating the next program group after receiving the patient input indicating the degree of efficacy.

10. The method of claim 8, further comprising receiving patient input naming a program group, and presenting the name of the program group to the patient via a display.

11. The method of claim 1, wherein one of the program groups is considered evaluated if it was used to deliver electrical stimulation therapy.

12. The method of claim 1, further comprising delivering the stimulation therapy via an implantable stimulator.

13. The method of claim 1, further comprising presenting an indication to the patient that one or more unevaluated program groups are available for evaluation.

14. The method of claim 1, wherein each of the program groups includes one or more programs, and each of the programs specifies one or more parameters for delivery of electrical stimulation therapy.

15. The method of claim 14, wherein the parameters include electrode combination, electrode polarity, stimulation current amplitude, stimulation voltage amplitude, stimulation pulse width and stimulation pulse rate.

16. The method of claim 1, further comprising marking one or more of the program groups with a subjective ranking specified by patient input.

17. The method of claim 1, further comprising delivering the stimulation therapy via an implantable stimulator, presenting the distinction via an external programmer that communicates with the implantable stimulator, and storing an indication of which program groups are unevaluated, which program groups are effective, and which program groups are ineffective in memory associated with the implantable stimulator at the direction of the external programmer.

18. The method of claim 1, wherein automatically hiding includes removing the program groups that have been previously evaluated by the patient from the list of electrical stimulation program groups for selection by the patient for delivery of electrical stimulation therapy so that the patient must choose another program group from the list for delivery of electrical stimulation therapy.

19. The method of claim 18, wherein automatically hiding includes removing one of the program groups from the list of electrical stimulation program groups for selection by the patient for delivery of electrical stimulation therapy in response to the patient evaluating the program group.

20. A programmer for use with an electrical stimulator, the programmer comprising:
a user interface that presents information to a user of the electrical stimulator; and
a processor that controls the user interface to present a list of electrical stimulation program groups for selection by a patient to deliver electrical stimulation therapy via an electrical stimulator, and automatically hides, from the list of electrical stimulation program groups, program groups that have been previously evaluated by the patient.

21. The programmer of claim 20, wherein the user interface receives patient input, and the processor controls the display to hide one of the program groups in response to patient input requesting that the program group be hidden.

22. The programmer of claim 20, wherein the user interface receives patient input, and the processor controls the display to unhide one of the program groups in response to patient input requesting that the program group be unhidden.

23. The programmer of claim 20, wherein the user interface receives patient input, and the processor prevents the patient from selecting one of the hidden program groups for delivery of stimulation therapy.

24. The programmer of claim 23, wherein the processor automatically selects the next group that has not been previously evaluated by the patient and delivers electrical stimulation therapy according to the next group.

25. The programmer of claim 20, wherein the user interface receives patient input, and the processor permits the patient to select unhidden program groups for delivery of stimulation therapy.

26. The programmer of claim 20, wherein the user interface receives patient input indicating a degree of efficacy of one or more of the evaluated program groups, and the processor controls the display to present an indication of the degree of efficacy to the patient via a display.

27. The programmer of claim 20, wherein one of the program groups is considered evaluated if it was used to deliver electrical stimulation therapy.

28. The programmer of claim 20, wherein the programmer controls the electrical stimulator to deliver the stimulation therapy to the patient.

29. The programmer of claim 20, wherein the programmer controls the user interface to present an indication to the patient that one or more unevaluated program groups are available for evaluation.

30. The programmer of claim 20, wherein each of the program groups includes one or more programs, and each of the programs specifies one or more parameters for delivery of electrical stimulation therapy, the parameters including electrode combination, electrode polarity, stimulation amplitude, stimulation pulse width and stimulation pulse rate.

31. The programmer of claim 20, wherein the user interface receives patient input specifying a subjective ranking of one or more of the program groups, the processor controlling the user interface to present an indication of the subjective ranking.

32. The programmer of claim 20, further comprising a telemetry interface that communicates with the stimulator, wherein the controller communicates with the stimulator to store and retrieve an indication of which program groups are unevaluated, which program groups are effective, and which program groups are ineffective in memory associated with the stimulator.

33. The programmer of claim 20, wherein the processor automatically hides the program groups that have been previously evaluated by the patient by removing the program groups from the list of electrical stimulation program groups for selection by the patient for delivery of electrical stimulation therapy so that the patient must choose another program group from the list for delivery of electrical stimulation therapy.

34. The programmer of claim 33, wherein the processor automatically hides a program group by removing one of the program groups from the list of electrical stimulation programs groups for selection by the patient for delivery of electrical stimulation therapy in response to the patient evaluating the program group.

35. A computer-readable storage medium comprising instructions to cause a processor to:
present a list of electrical stimulation program groups for selection by a patient to deliver electrical stimulation therapy via an electrical stimulator; and
automatically hide, from the list of electrical stimulation program groups, program groups that have been previously evaluated by the patient.

36. The computer-readable storage medium of claim 35, wherein the instructions cause the processor to hide one of the program groups in response to patient input requesting that the program group be hidden, and unhide one of the program groups in response to patient input requesting that the program group be unhidden.

37. The computer-readable storage medium of claim 36, wherein the instructions cause the processor to prevent the patient from selecting one of the hidden program groups for delivery of stimulation therapy, and permit the patient to select unhidden program groups for delivery of stimulation therapy.

38. The computer-readable storage medium of claim 35, wherein each of the program groups includes one or more programs, and each of the programs specifies one or more parameters for delivery of electrical stimulation therapy, wherein the parameters include electrode combination, electrode polarity, stimulation amplitude, stimulation pulse width and stimulation pulse rate.

39. The computer-readable storage medium of claim 35, wherein the instructions cause the processor to automatically hide the program groups that have previously been evaluated by the patient from the list of electrical stimulation program groups for selection by the patient for delivery of electrical stimulation therapy so that the patient must choose another program group from the list for delivery of electrical stimulation therapy.

40. The computer-readable storage medium of claim 39, wherein the instructions cause the processor to automatically hide a program group by removing one of the program groups from the list of electrical stimulation program groups for selection by the patient for delivery of electrical stimulation therapy in response to the patient evaluating the program group.

41. A system comprising:
   an implantable electrical stimulator that delivers electrical stimulation therapy to a patient; and
   an external programmer including a user interface that presents information to a user of the electrical stimulator, and a processor that controls the user interface to present a list of electrical stimulation program groups for selection by a patient to deliver electrical stimulation therapy via an electrical stimulator, and automatically hides, from the list of electrical stimulation program groups, program groups that have been previously evaluated by the patient.

42. The system of claim 41, wherein the user interface of the external programmer includes a display.

* * * * *